United States Patent [19]
Kulkarni

[11] Patent Number: 5,133,346
[45] Date of Patent: Jul. 28, 1992

[54] APNEA MONITOR DATA SYSTEM

[75] Inventor: Chandrakumar D. Kulkarni, Battle Creek, Mich.

[73] Assignee: Arvee Medical, Incorporated, Battle Creek, Mich.

[21] Appl. No.: 804,490

[22] Filed: Dec. 9, 1991

Related U.S. Application Data

[63] Continuation of Ser. No. 620,740, Dec. 3, 1990, abandoned.

[51] Int. Cl.$^5$ ............................................. A61M 16/00
[52] U.S. Cl. ........................... 128/202.22; 128/205.23; 128/716
[58] Field of Search ...................... 128/204.21, 204.23, 128/205.23, 202.22, 716, 722, 723; 364/413.03

[56] References Cited

U.S. PATENT DOCUMENTS

| | | | |
|---|---|---|---|
| 3,923,055 | 12/1975 | Hammacher | 128/204.23 |
| 3,972,320 | 8/1976 | Kalman | 364/413.03 |
| 4,036,221 | 7/1977 | Hillsman et al. | 128/204.23 |
| 4,053,951 | 10/1977 | Hudspeth et al. | 364/413.03 |
| 4,444,201 | 4/1984 | Itoh | 128/205.23 |
| 4,484,578 | 11/1984 | Durkan | 128/205.23 |
| 4,619,269 | 10/1986 | Cutler et al. | 128/205.23 |
| 4,671,297 | 6/1987 | Schulze, Jr. | 128/204.23 |
| 4,972,842 | 11/1990 | Korten et al. | 128/204.23 |

*Primary Examiner*—Edgar S. Burr
*Assistant Examiner*—Aaron J. Lewis
*Attorney, Agent, or Firm*—Beaman & Beaman

[57] ABSTRACT

An apnea monitoring system which utilizes a portable data storage cartridge for storing the monitored events and waveforms of a patient's respiration, ECG and the like. The cartridge is easily carried or mailed to a remote location and connected to a transfer unit to provide a cost-effective and time-efficient method of transferring the stored information to a computer for displaying selected events and waveforms. The monitor includes provisions for indicating the available memory space on the cartridge, and the cartridge is replaceable to provide an unlimited amount of memory space and permit continued use of the monitor during transferring of information to a computer.

1 Claim, 1 Drawing Sheet

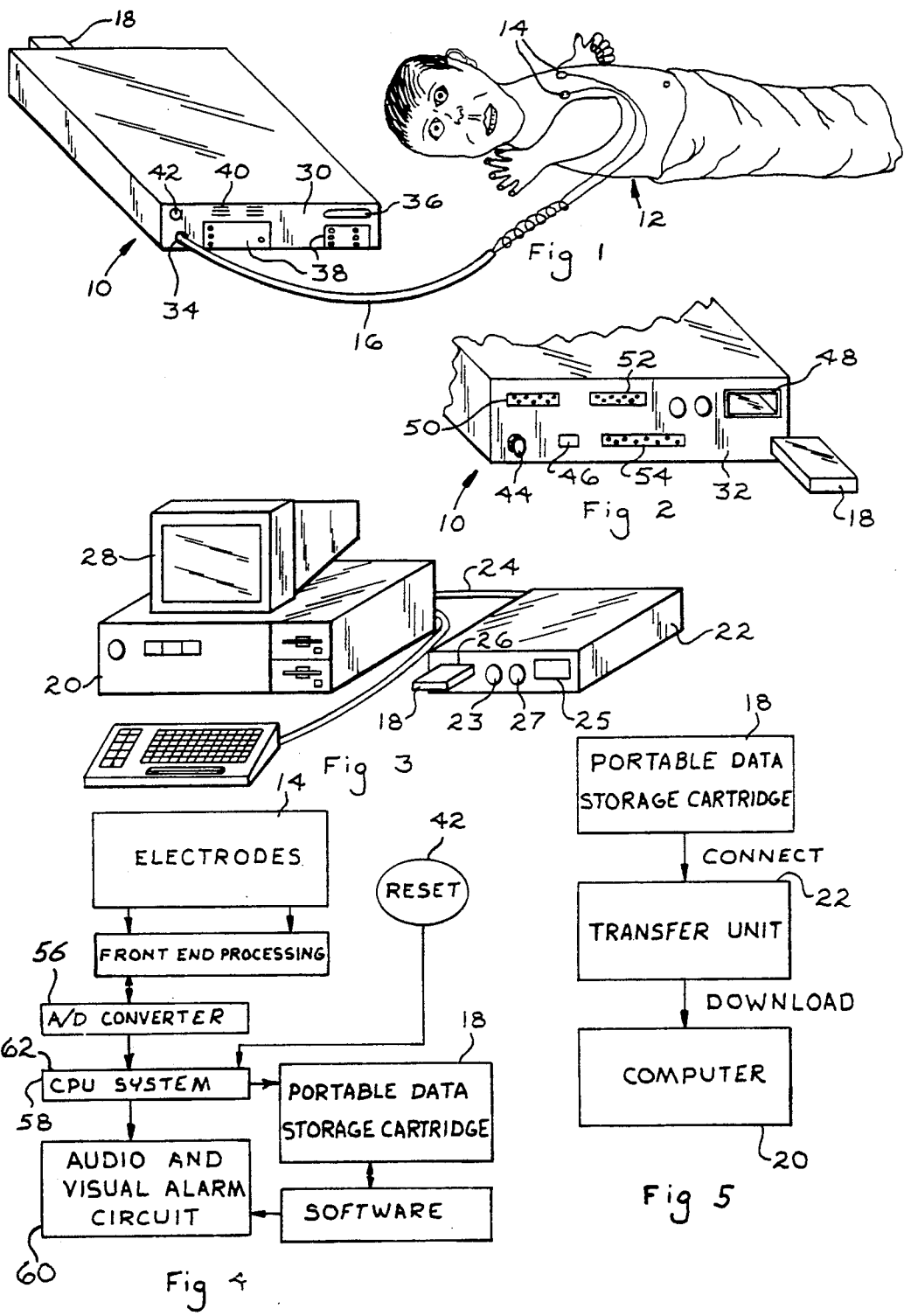

APNEA MONITOR DATA SYSTEM

This application is a continuation of application Ser. No. 620,740 filed Dec. 3, 1990, now abandoned.

BACKGROUND OF THE INVENTION

Apnea monitoring systems are utilized to monitor a patient's respiration and heart rate (ECG) to warn the caregiver in the event of breathing interruptions and/or slowed or rapid heart rate. Electrodes located on either side of the patient's thoracic cavity measure respiration and detect the actual electrical signal of the heart to pick up the ECG. The detected events and waveforms are compared to preset values which represent normal respiration and heart rate events. Upon detection of the preset values being exceeded, signals are transmitted to audio and visual alarms for indicating to the caregiver that an abnormal event has occurred.

The newer apnea monitoring systems are provided with internal memory for storing the monitored events and waveforms. The stored information is downloaded to a computer which permits selected events and waveforms to be displayed or printed for analysis purposes. However, the monitor must be transported and connected to the computer, or the computer transported to the monitor, which is time consuming and costly. Often, the monitor is utilized in the patient's home and must be transported back to the doctor's office or hospital, and, if continued monitoring is required, another monitor is needed in place of the one being transported. Such monitors also have limited memory space, and downloading of the stored information to the computer is relatively slow.

It is an object of the invention to provide an apnea monitoring system wherein the monitored events and waveforms are stored on a portable data storage device to provide a cost-effective and time-efficient method of transferring the stored information to a computer.

Another object of the invention is to provide an apnea monitoring system which utilizes a portable data storage cartridge wherein the cartridge is adapted to be connected to a transfer unit which facilitates quick downloading of the stored information to a computer.

A further object of the invention is to provide an apnea monitoring system which utilizes a portable data storage cartridge which is easily carried or mailed to provide a convenient method of transferring the stored information to a computer such as when the monitor is used in the patient's home and the computer is remotely located in the doctor's office or hospital.

Yet a further object of the invention is to provide an apnea monitoring system which utilizes a portable data storage cartridge which is replaceable to provide an unlimited amount of memory space and permit continued use of the monitor during the transfer of the stored information to a computer.

Another object of the invention is to provide an apnea monitoring system which utilizes a portable data storage cartridge wherein the monitor is provided with provisions for indicating the available memory space on the cartridge and when the cartridge needs replacing.

In the practice or the invention, the apnea monitoring system is utilized to monitor a patient's respiration and ECG to provide a warning to the caregiver in the event of breathing interruptions and/or rapid or slowed heart rate. Electrodes are located on either side of the patient's chest to measure the respiration and pick up the heart rate as is known. The detected events and waveforms are compared to preset values which correspond to the normal respiration and ECG of the patient. Visual and audio alarm circuits provide means for indicating to the caregiver when an abnormal event is detected so that immediate attention may be given to the patient.

The monitored events and waveforms are stored on a portable data storage cartridge which permits the information to be conveniently transferred to a computer. The cartridge is releasably inserted in a cartridge holder which is exteriorly mounted on the monitor and interfaced with the monitor's circuitry. Software monitors the memory space on the cartridge. Visual and audio means are provided for indicating the available memory space and when the cartridge needs replacing.

To transfer the stored information to a computer, the cartridge is simply removed from the monitor and connected to a transfer unit. The transfer unit is interfaced with a computer and facilitates quick downloading of the stored information for displaying or printing selected events and waveforms. If desired, the stored information may be saved on the cartridge, or the memory may be cleared to permit the cartridge to be reused.

The cartridge is easily carried or mailed which provides a time-efficient and cost-effective method of transferring the stored information to a computer in that neither the computer nor the monitor need be transported. Also, the cartridge is replaceable which provides an unlimited amount of memory space and permits continued use of the monitor when information on one cartridge is being transferred to a computer.

BRIEF DESCRIPTION OF THE DRAWINGS

The aforementioned objects and advantages of the invention will be appreciated from the following description and accompanying drawings wherein:

FIG. 1 is a perspective view illustrating an apnea monitoring system incorporating the inventive concepts in a typical application wherein the monitored events and waveforms are stored on a portable data storage cartridge, FIG. 2 is a perspective view illustrating the rear panel of the monitor prior to inserting the cartridge in the cartridge holder, FIG. 3 is a perspective view illustrating a typical application wherein the cartridge is connected to the transfer unit for downloading the stored information to a computer, FIG. 4 is a schematic block diagram representing a typical circuit layout of the monitor of FIGS. 1 and 2, and FIG. 5 is a schematic block diagram illustrating the steps involved for transferring the stored information from the cartridge to the computer.

DESCRIPTION OF THE PREFERRED EMBODIMENT

In FIG. 1, a typical application is shown wherein an apnea monitoring system 10 incorporating the inventive concepts of the invention is utilized to monitor the respiration and heart rate (ECG) of a patient 12 to provide a warning to a caregiver in the event of slowed or rapid heart rate and/or breathing interruptions.

The monitor 10 utilizes a pair of electrode patches 14 located on either side of the patient's thoracic cavity to measure the respiration and detect the actual electrical signal of the heart for picking up the ECG as is known. The electrodes 14 are connected via a cable 16 to an isolated input on the monitor for transmitting the detected events and waveforms to internal circuitry for monitoring as later described. The monitored events and waveforms are stored on a portable data storage device or cartridge 18 which permits the stored information to be conveniently transferred to a separate computer for analysis purposes.

In FIG. 3, a typical application is shown wherein the information on the cartridge 18 is being transferred to a computer 20. The cartridge 18 is connected to a transfer unit 22 which is interfaced to the computer 20 via a cable 24. The transfer unit 22 includes a power switch 23, a liquid crystal display 25, and a cartridge holder 26, wherein the cartridge 18 inserted. The holder 26 is interfaced with a solid state circuit, not illustrated, which facilitates quick downloading of the stored information t the computer 20 for viewing selected events and waveforms on the display 28 or printing on a printer, not shown. A button 27 enables the transfer unit for downloading when depressed.

The exterior components of the monitor 10 will be appreciated in FIGS. 1 and 2 and are interfaced with internal circuitry later described and appreciated in the schematic block diagram of FIG. 4. The monitor 10 includes a front panel 30 and a rear panel 32. The front panel includes an isolated input 34 which connects to the cable 16 for receiving the detected events and waveforms. A liquid crystal display 36, lights 38, and a speaker 40 provide audio and visual alarm means for indicating both the status of the patient and the monitor, and a reset button 42 provides means for clearing the alarm light indicating when conditions are normal.

The rear panel 32 is provided with a power switch 44 for energizing the monitor 10 and an a.c. power receptacle 46 for receiving a cord, not shown, to supply power to the monitor and/or charge an internal battery. A cartridge holder 48 is mounted in the rear panel 32 wherein the cartridge 18 is adapted to be inserted for interfacing with the internal circuitry. Inputs 50 and 52 are adapted to receive auxiliary connectors. An output connector 54 contains outputs for ECG, respiration and alarms.

The basic operation of the monitor 10 will be appreciated in the schematic block diagram of FIG. 4 which represents a typical circuit in accord with the inventive concepts for monitoring and storing events and waveforms of a patient's respiration and ECG on the portable cartridge.

The electrodes 14 detect the patient's respiration and ECG events and waveforms. The detected events and waveforms are analog signals and are processed and converted to digital form through an analog-to-digital convertor 56. The digital signals are stored on the memory of the cartridge 18 which is of solid state, and are compared to preset values by the software. The preset values correspond to the normal respiration and heart rate of a patient. Upon detection of the preset values being exceeded, the comparator 58 transmits the necessary control signals to the audio and visual alarm circuit 60, which includes the display 36, lights 38, and speaker 40, for visually and audibly indicating to the caregiver that the patient is experiencing an abnormal event. At this time, the waveforms are stored on the memory of the cartridge 18 to indicate details of the alarm condition.

During operation, a microprocessor system continuously monitors the memory status of the cartridge 18. The microprocessor system is interfaced with the alarm circuit 60 for indicating the available memory remaining on the cartridge and when the cartridge 18 is full and needs replacing. After downloading to the computer, the information stored on the memory of the cartridge may be cleared to permit the cartridge to be reused, or may be saved for transferring to a computer when desired.

In FIG. 5, a schematic block diagram illustrates the steps involved in transferring the stored information from the cartridge 18 to the computer 20. The cartridge 18 is connected to the transfer unit 22 which is interfaced with the computer 20. Once the cartridge 18 is connected, the information is downloaded to the computer whereby selected events and waveforms may be displayed or printed for analysis purposes.

The cartridge 18 is of a concise dimension which permits the cartridge to be easily carried or mailed to a remote location. This provides a cost-effective and time-efficient method of transferring the stored information to a computer in that neither the monitor nor the computer needs to be transported as is necessary in conventional types of apnea monitoring systems wherein the memory resides in the monitor. As the cartridge is replaceable, an unlimited amount of memory space is available and continued use of the monitor 10 may be maintained when information is being transferred to a computer.

The invention is particularly advantageous in applications wherein apnea monitoring is performed in the patient's home as the cartridge may be carried or mailed back to the doctor's office or hospital. This eliminates the necessity of having to transport and replace the monitor itself which provides a convenience and reduces costs.

It is appreciated that various modifications to the inventive concepts may be apparent to those skilled in the art without departing from the spirit and scope of the invention.

I claim:

1. An apnea monitoring system comprising, in combination, apnea electronic monitoring means for monitoring the events and waveforms of a patient's respiration and producing analog electronic signals representing said events and waveforms, visual and audio alarm means associated with said monitoring means visually and audibly indicating pre-determined abnormalities in said events and wave forms, electronic means associated with said monitor means converting said analog electronic signals to digital electronic signals, a portable data storage device connectable to said monitoring means and detachably associated therewith having a memory for storing said digital electronic signals representing said monitored events and waveforms receiving and storing said digital electronic signals from said monitor, and data storage device monitoring means associated with said apnea electronic monitoring means sensing said device's memory to determine the available memory remaining on said device, and indicating means operatively connected to said data storage device monitoring means interfaced with said visual and audible alarm means selectively visually and audibly indicating the status of said device's memory, said device adapted to be interfaced with a computer separate and remote from said monitor for transferring said stored events and waveforms digital signals thereto.

* * * * *